United States Patent [19]
Melin

[11] Patent Number: 5,962,056
[45] Date of Patent: Oct. 5, 1999

[54] PROCESS FOR PURIFYING OLIVE OIL

[75] Inventor: Christian Melin, Verriéres le Buisson, France

[73] Assignee: Baxter International Inc., Deerfield, Ill.

[21] Appl. No.: 08/121,663

[22] Filed: Sep. 15, 1993

Related U.S. Application Data

[63] Continuation of application No. 07/562,413, Aug. 2, 1990, abandoned, which is a continuation of application No. 07/222,810, Jul. 22, 1988, abandoned.

[30] Foreign Application Priority Data

Jul. 23, 1997 [FR] France ................................. 87 10404

[51] Int. Cl.⁶ ..................................................... A63D 7/00
[52] U.S. Cl. ...................... 426/417; 426/330.6; 554/175
[58] Field of Search ............................. 426/330.6, 602, 426/417; 554/175

[56] References Cited

U.S. PATENT DOCUMENTS

| | | | |
|---|---|---|---|
| 2,199,364 | 4/1940 | Musher | 426/330.6 |
| 2,221,404 | 11/1940 | Musher | 426/330.6 |
| 2,838,553 | 6/1958 | Ayres | 260/425 |
| 2,917,525 | 12/1959 | Thurman | 260/425 |
| 3,102,898 | 9/1963 | Schmitt | 260/425 |
| 4,497,800 | 2/1985 | Larson | 426/74 |
| 4,816,189 | 3/1989 | Rothbart | 260/425 |

FOREIGN PATENT DOCUMENTS

| | | |
|---|---|---|
| 891271 | 3/1944 | France . |
| 110832 | 3/1967 | Norway . |
| 351860 | 12/1972 | Sweden . |
| 642751 | 9/1950 | United Kingdom . |

OTHER PUBLICATIONS

Lewkowitsch 1922 Chemical Technology and Analysis of Oils Fats and Wafers Sixth Edition Macmillan & Co. Ltd. London pp. 344–365.

Singleton 1966 JAOCS 43(10) 592.

*Primary Examiner*—Carolyn Paden
*Attorney, Agent, or Firm*—Hill & Simpson

[57] ABSTRACT

A process for purifying olive oil which includes neutralizing the oil with an amount of a saturated aqueous solution of crystalline disodium carbonate equivalent to two to ten times the weight of oleic acid in the oil calculated after assay; allowing the aqueous phase to separate and washing the oil until the oil is substantially neutral; and drying the oil and decolorizing the oil using a bleaching earth under an inert atmosphere.

4 Claims, No Drawings

PROCESS FOR PURIFYING OLIVE OIL

This is a continuation of application Ser. No. 07/562,413 filed Aug. 2, 1990, now abandoned which in turn is a continuation of application Ser. No. 07/222,810, filed Jul. 22, 1988 now abandoned.

The present invention relates to a process for purifying olive oil, to olive oil obtained by this process and to an emulsion containing the olive oil.

The process of the invention enables a purified olive oil, suitable to use as an enteral or parenteral foodstuff, to be obtained, for example from an extra virgin olive oil extracted in a first pressing.

The oil obtained is an olive oil which is of very low free acidity, non-oxidized and free from pigments responsible for colouration.

The oil obtained has nutritional qualities superior to the virgin olive oil described in the European Pharmacopoeia, 2nd edition, Part II.10.

The oil obtained according to the process of the invention may be used in emulsions which may be administered to a subject enterally or parenterally, for example in emulsions as described by the Applicant in its French Patent Applications Nos. 87/10,407 and 87/10,405.

The present invention provides a process for purifying olive oil which comprises:

neutralizing the oil with an amount of a saturated aqueous solution of alkaline carbonate (disodium or dipotassium) equivalent to two to ten times the weight of oleic acid in the oil calculated after assay;

allowing the aqueous phase to separate and washing the oil until complete neutrality; and drying the oil and decolourizing the oil using a bleaching earth under an inert atmosphere.

The initial olive oil is preferably an oil as defined in the European Pharmacopoeia. The amount of the saturated aqueous solution of alkaline carbonate used is preferably equivalent to two to three times, more preferably about two and a half times, the weight of oleic acid in the oil calculated after assay. The neutralization step is preferably carried out under an inert atmosphere, generally at a temperature of from 20 to 80° C., preferably from 40 to 50° C., with stirring.

In the washing step, the oil is preferably washed with distilled water.

The amount of bleaching earth used in the decolourization step is preferably from 1 to 10% by weight, more preferably from 5 to 8% by weight, based on the weight of the neutralized oil. The inert atmosphere is generally nitrogen. The oil is preferably kept in contact with the earth at a temperatue of from 20 to 80° C., more preferably from 50 to 60° C., for from 30 to 40 minutes, with slow stirring, for example stirring at 100 to 500 r.p.m.

The oil obtained may, if appropriate, be deodorized at a low temperature, for example at <190° C., preferably under a high vacuum, for example approximately $10^{-3}$ torr (0.133 Pa).

The Example which follows further illustrates the present invention.

EXAMPLE

Olive oil corresponding to the definition in the European Pharmacopoeia is neutralized at 45° C. with an amount of a saturated aqueous solution of disodium carbonate equivalent to 2.5 times the weight of oleic acid in the oil. The oil is then washed twice with distilled water and dried. The oil is decolourized by adding 6% by weight of a bleaching earth for 35 min at 60° C. under nitrogen. The oil is deodorized for 60 min at 180° C., using steam, under a vacuum of $10^{-3}$ torr (0.133 Pa). The comparative features of two olive oils, one corresponding to the definition in the European Pharmacopoeia and the other purified according to the process of the invention in the Example, are shown in Table 1.

The olive oil obtained according to the process of the invention has a very low free acidity, a very low peroxide value and a virtually complete absence of pigments (xanthophyll carotenoids and chlorophylls).

TABLE

|  | Olive oil Europ. Ph. 2nd edition II.10 | Olive oil purified according to the process of the invention |
|---|---|---|
| Density | 0.910–0.916 | 0.910–0.916 |
| U.V. absorbance $E\% \dfrac{232 \text{ nm}}{270 \text{ nm}}$ | >8 | <3 |
| Acid value | ≦2.0 | ≦0.2 |
| Peroxide value | ≦15.0 | ≦1.0 |
| Triglyceride and sterol composition |  | Identical |
| Vis. absorbance at 382 nm | Absence of standard | ≦0.80 |
| 460 nm | Absence of standard | ≦0.02 |
| 485 nm | Absence of standard | ≦0.02 |
| 660 nm | Absence of standard | ≦0.02 |

I claim:

1. A process for making a purified olive oil for use in enteral and parenteral nutritional formulations, the method comprising:

providing an olive oil sample to be purified having a previously determined oleic acid content;

neutralizing the oleic acid present in the oil by contacting the oil sample with an amount of a saturated aqueous solution of alkaline carbonate equivalent to two to ten times the weight of oleic acid present in the oil sample, allowing an aqueous phase to separate and washing the oil with water until complete neutrality to provide a neutralized oil sample; and drying and decolouring the neutralized oil sample by contacting the neutralized oil sample with bleaching earth under an inert atmosphere at a temperature of between about 20° C. to about 80° C. to provide a purified oil product having an acceptably low amount of peroxides, free acids and pigments for enteral and parenteral nutritional administration.

2. A process according to claim 1 wherein the oil obtained is deodorized at a low temperature.

3. A process according to claim 1 wherein the amount of the saturated aqueous solution of disodium carbonate is equivalent to two to three times the weight of oleic acid in the oil.

4. A process according to claim 3 wherein the amount of the saturated aqueous solution of disodium carbonate is equivalent to about two and a half times the weight of the oleic acid in the oil.

* * * * *